US009020583B2

(12) United States Patent
Zhang

(10) Patent No.: US 9,020,583 B2
(45) Date of Patent: Apr. 28, 2015

(54) PATIENT SIGNAL ANALYSIS AND CHARACTERIZATION

(71) Applicant: Siemens Medical Solutions USA, Inc., Malvern, PA (US)

(72) Inventor: Hongxuan Zhang, Palatine, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 0 days.

(21) Appl. No.: 14/190,276

(22) Filed: Feb. 26, 2014

(65) Prior Publication Data

US 2014/0276156 A1    Sep. 18, 2014

Related U.S. Application Data

(60) Provisional application No. 61/778,868, filed on Mar. 13, 2013.

(51) Int. Cl.
*A61B 5/0472* (2006.01)
*A61B 5/04* (2006.01)
*A61B 5/0456* (2006.01)
*A61B 5/046* (2006.01)
*A61B 5/00* (2006.01)
*A61B 5/0452* (2006.01)
*A61N 1/362* (2006.01)

(52) U.S. Cl.
CPC .......... *A61B 5/04012* (2013.01); *A61B 5/0456* (2013.01); *A61B 5/046* (2013.01); *A61B 5/0472* (2013.01); *A61B 5/04525* (2013.01); *A61B 5/7264* (2013.01); *A61N 1/3621* (2013.01)

(58) Field of Classification Search
None
See application file for complete search history.

(56) References Cited

U.S. PATENT DOCUMENTS

| | | | |
|---|---|---|---|
| 4,023,564 A * | 5/1977 | Valiquette et al. | 600/517 |
| 4,681,117 A | 7/1987 | Brodman et al. | |
| 4,798,211 A | 1/1989 | Goor et al. | |
| 4,924,875 A | 5/1990 | Chamoun | |
| 4,930,075 A | 5/1990 | Kortas | |
| 5,054,496 A | 10/1991 | Wen et al. | |
| 5,159,932 A | 11/1992 | Zanetti et al. | |
| 5,365,426 A | 11/1994 | Siegel et al. | |
| 6,024,705 A | 2/2000 | Schlager et al. | |
| 6,112,116 A | 8/2000 | Fischell et al. | |
| 6,339,720 B1 | 1/2002 | Anzellini et al. | |
| 6,368,284 B1 | 4/2002 | Bardy | |
| 6,424,860 B1 | 7/2002 | Karlsson et al. | |
| 6,468,263 B1 | 10/2002 | Fischell et al. | |
| 6,501,983 B1 | 12/2002 | Natarajan et al. | |
| 6,663,572 B2 | 12/2003 | Starobin et al. | |
| 7,072,708 B1 | 7/2006 | Andresen et al. | |
| 7,181,268 B2 | 2/2007 | Sheldon et al. | |
| 7,225,013 B2 | 5/2007 | Geva et al. | |
| 7,225,015 B1 | 5/2007 | Min et al. | |
| 7,231,244 B2 | 6/2007 | Laitio et al. | |
| 7,266,410 B2 | 9/2007 | Chen | |
| 7,277,745 B2 | 10/2007 | Natarajan et al. | |

(Continued)

*Primary Examiner* — Kennedy Schaetzle

(57) ABSTRACT

Disclosed herein is a framework for facilitating patient signal analysis. In accordance with one aspect, at least one region of interest within a cycle of a waveform of patient signal data is identified. The identified region of interest may be segmented into portions using amplitude percentage categories. A sequential morphological data series may be generated by compiling time intervals of the segmented portions. One or more sequential signal parameters may be calculated based on the sequential morphological data series. A report may then be generated based at least in part on the one or more sequential signal parameters.

20 Claims, 6 Drawing Sheets

(56) References Cited

U.S. PATENT DOCUMENTS

| | | | |
|---|---|---|---|
| 7,343,198 B2 * | 3/2008 | Behbehani et al. | 600/509 |
| 7,361,473 B2 | 4/2008 | Valkirs et al. | |
| 7,415,307 B2 | 8/2008 | Sharma et al. | |
| 7,654,965 B2 | 2/2010 | Morganroth | |
| 7,813,792 B2 | 10/2010 | Xue et al. | |
| 7,904,153 B2 | 3/2011 | Greenhut et al. | |
| 7,969,864 B2 | 6/2011 | Nylander et al. | |
| 7,996,070 B2 * | 8/2011 | van Dam et al. | 600/509 |
| 8,010,347 B2 | 8/2011 | Ricci et al. | |
| 8,024,030 B2 | 9/2011 | Douglas et al. | |
| 8,160,687 B2 | 4/2012 | Warren et al. | |
| 8,249,704 B2 | 8/2012 | Armoundas et al. | |
| 8,265,739 B1 | 9/2012 | Boileau et al. | |
| 8,768,459 B2 * | 7/2014 | Ghosh et al. | 607/4 |
| 2002/0183640 A1 * | 12/2002 | Bjorling | 600/517 |
| 2007/0093720 A1 * | 4/2007 | Fischell et al. | 600/509 |
| 2007/0276264 A1 * | 11/2007 | Eide | 600/485 |

\* cited by examiner

PATIENT SIGNAL ANALYSIS AND CHARACTERIZATION

CROSS-REFERENCE TO RELATED APPLICATION

This application claims the benefit of U.S. provisional application No. 61/778,868 filed Mar. 13, 2013, the entire contents of which are incorporated herein by reference.

TECHNICAL FIELD

The present disclosure generally relates to systems and methods for analyzing and characterizing patient signals.

BACKGROUND

Cardiac arrhythmia is a condition in which the electrical activity of the heart is irregular or is faster or slower than normal. Cardiac arrhythmia may be classified by rate and/or mechanism. For instance, atrial fibrillation (AF) is the most common type of serious arrhythmia that involves a very fast and irregular contraction of the atria. Ventricular fibrillation (VF) is a condition in which there is uncoordinated contraction of the cardiac muscle of the ventricles in the heart. Myocardial ischemia (MI) is a type of arrhythmia that occurs when blood flow to the heart muscle is decreased by a partial or complete blockage of the heart's arteries. Myocardial infarction (commonly known as a heart attack) occurs when blood stops flowing properly to part of the heart and the heart muscle is injured due to not receiving enough oxygen. This can lead to irreversible scarring and necrosis of the muscle tissue, reducing the efficiency with which the heart can pump blood to the rest of the body and possibly leading to fatal cardiac arrhythmia.

Cardiac functional abnormality and arrhythmia usually slow down tissue performance (e.g., contracting and reperfusion) and reduce blood flow to regions of the heart. Cells respond by altering the action potentials. The changes in these individual cells manifest in electrograms during depolarization and repolarization, reducing signal energy (hyperkalemia or anoxia) or creating multi-phasic waveform, particularly distortions in the electrophysiological response morphology. Electrophysiological (EP) response and activity analysis is routinely used to manage such cardiac arrhythmias, disorders and irregularities. The 12-lead electrocardiogram (ECG) and multi-channel intra-cardiac electrograms (ICEG) are generally regarded as the diagnostic reference standard for evaluating cardiac rhythm and events.

Currently, waveform morphologies and time-domain parameter analysis, such as P wave, QRS complex, ST segment, T wave, are used for cardiac arrhythmia monitoring and identification. However, such analysis is sometimes subjective and time-consuming, and requires extensive medical expertise and clinical experience for accurate interpretation and proper cardiac rhythm management. Inaccurate and subjective evaluation and diagnosis may cause unexpected delays in cardiac rhythm management, such as drug delivery and emergency treatment.

Most traditional clinical methods and approaches are performed for qualitative testing and diagnosis of cardiac pathology (e.g., 0.1 mV of ST segment elevation for myocardial ischemia event detection). There is currently no known efficient, convenient, reliable and sensitive method to perform both quantitative and qualitative characterization and evaluation of cardiac signal waveform and morphology, especially for early detection and diagnosis of cardiac events. In addition, known clinical approaches may not be efficiently applicable and useful in some cases. For example, myocardial ischemia and infarction are usually detected by ST segment voltage deviation (e.g., 0.1 mV deviation). However, this method only works for surface ECG signals, but not intra-cardiac electrograms (ICEG) signals.

Accordingly, there exists a need to provide an improved framework to address these deficiencies and related problems.

SUMMARY

The present disclosure relates to a framework for facilitating patient signal analysis. In accordance with one aspect, at least one region of interest within a cycle of a waveform of patient signal data is identified. The identified region of interest may be segmented into portions using amplitude percentage categories. A sequential morphological data series may be generated by compiling time intervals of the segmented portions. One or more sequential signal parameters may be calculated based on the sequential morphological data series. A report may then be generated based at least in part on the one or more sequential signal parameters.

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Furthermore, it should be noted that the same numbers are used throughout the drawings to reference like elements and features.

DETAILED DESCRIPTION

Figure 1:
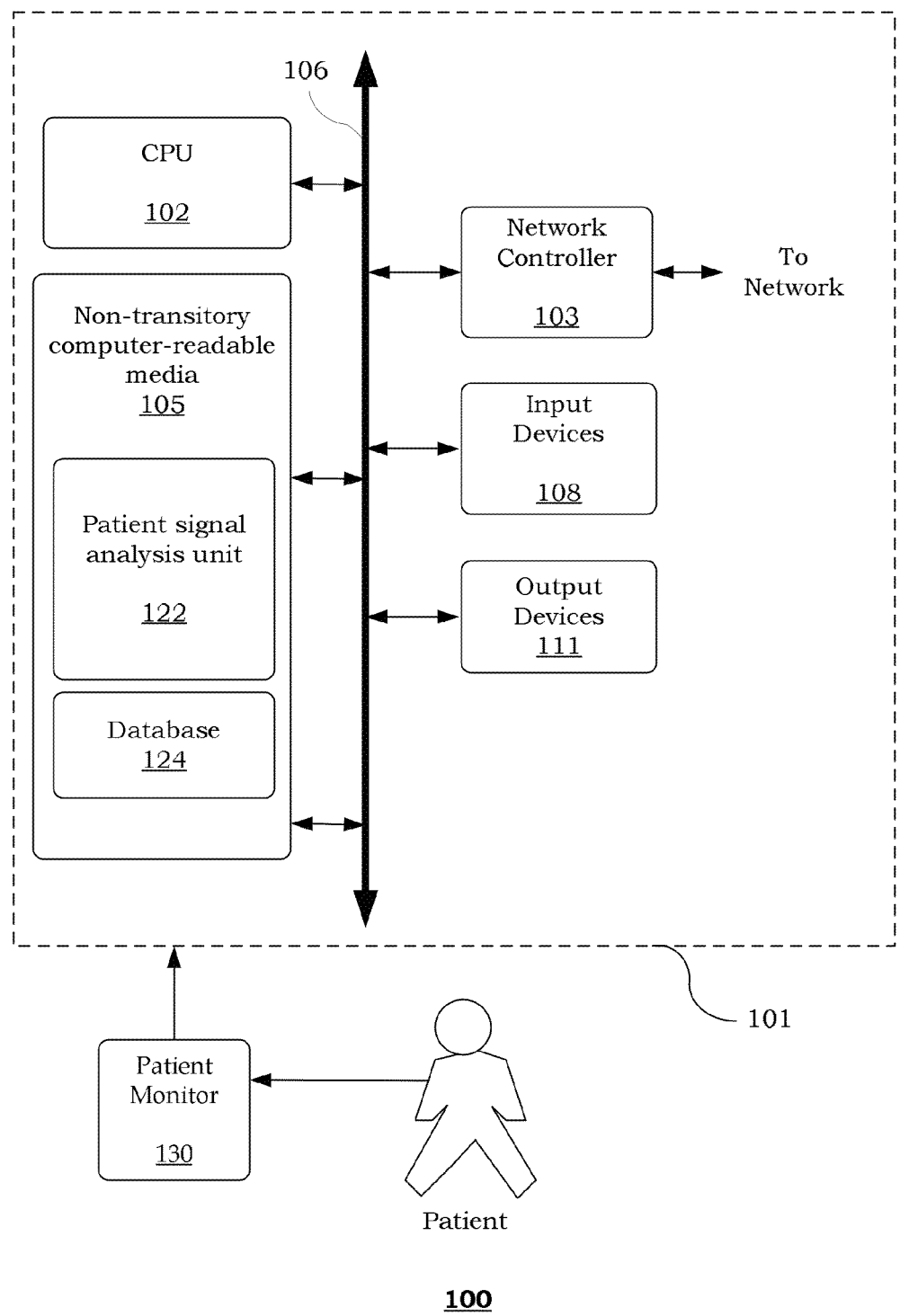
FIG. 1 shows an exemplary system.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

It is to be understood that the system and methods described herein may be implemented in various forms of hardware, software, firmware, special purpose processors, or a combination thereof. Preferably, the present invention is implemented in software as an application (e.g., n-tier application) comprising program instructions that are tangibly embodied on one or more program storage devices (e.g., magnetic floppy disk, RAM, CD ROM, ROM, etc.), and executable by any device or machine comprising suitable architecture. If written in a programming language conforming to a recognized standard, sequences of instructions designed to implement the methods can be compiled for execution on a variety of hardware platforms and for interface to a variety of operating systems. In addition, embodiments of the present framework are not described with reference to any particular programming language. It will be appreciated that a variety of programming languages may be used to implement embodiments of the present invention.

It is to be further understood that since the constituent system modules and method steps depicted in the accompanying Figures are preferably implemented in software, the actual connections between the system components (or the flow of the process steps) may differ depending upon the manner in which the present invention is programmed Given the teachings herein, one of ordinary skill in the related art will be able to contemplate these and similar implementations or configurations of the present invention.

The present framework provides a methodology to analyze patient signals based on quantized signal waveform and interval analysis. Examples of patient signals include cardiac electrophysiological signals, such as surface ECG and intra-cardiac electrograms (ICEG) signals. In accordance with some implementations, quantized cardiac signal waveform, interval measurements and sequential cardiac morphology parameters (e.g., unilateral and bilateral sequential ratios) are derived to advantageously facilitate a set of quantitative and qualitative techniques for early and more precise detection and characterization of cardiac pathologies and events, particularly for critical care monitoring and implant cardiac devices.

Furthermore, by using statistical calculation and computation, such as sequential morphology variability, variation, etc., cardiac electrophysiological activities and functions can advantageously be qualitatively and quantitatively estimated, characterized and derived with better sensitivities and stability, especially in noisy conditions. The present framework may be used to efficiently, accurately and reliably identify cardiac disorders, differentiate cardiac arrhythmias, characterize pathological severities, predict life-threatening events, and even evaluate drug delivery effects and/or provide treatment suggestions and/or evaluations. These and other features and advantages will be described in more detail herein.

For purposes of illustration, the present framework is described herein in the context of electrocardiography signal analysis for heart function characterization, detection and/or diagnosis. However, it should be appreciated that the present framework is also useful for analyzing other types of electrophysiological signals originating from other parts of the body, including but not limited to, the brain, muscles, eyes, auditory system and so forth. In addition, the present framework may also be used for analysis of other types of patient signals, including capnograph waveforms, saturation of peripheral oxygen (SPO2) signals, blood pressure signals, etc.

FIG. 1 shows an exemplary system 100 for implementing a method and system of the present disclosure. It is to be understood that, because some of the constituent system components and method steps depicted in the accompanying figures can be implemented in software, the actual connections between the systems components (or the process steps) may differ depending upon the manner in which the present framework is programmed. For example, the system 100 may be implemented in a client-server, peer-to-peer (P2P) or master/slave configuration. In such configurations, the system 100 may be communicatively coupled to other systems or components via a network, such as an Intranet, a local area network (LAN), a wide area network (WAN), a P2P network, a global computer network (e.g., Internet), a wireless communications network, or any combination thereof. Given the teachings of the present invention provided herein, one of ordinary skill in the related art will be able to contemplate these and similar implementations or configurations of the present invention.

As shown in FIG. 1, the system 100 includes a computer system 101 and a patient monitor 130. The computer system 101 may include, inter alia, a central processing unit (CPU) 102, a non-transitory computer-readable media 105, one or more output devices 111 (e.g., printer, display monitor, projector, speaker, etc.), a network controller 103, an internal bus 106 and one or more input devices 108, for example, a keyboard, mouse, touch screen, gesture and/or voice recognition module, etc. Computer system 101 may further include support circuits such as a cache, a power supply, clock circuits and a communications bus. Various other peripheral devices, such as additional data storage devices and printing devices, may also be connected to the computer system 101.

The present technology may be implemented in various forms of hardware, software, firmware, special purpose processors, or a combination thereof, either as part of the microinstruction code or as part of an application program or software product, or a combination thereof, which is executed via the operating system. In one implementation, the techniques described herein may be implemented as computer-readable program code tangibly embodied in non-transitory computer-readable media 105. Non-transitory computer-readable media 105 may include random access memory (RAM), read only memory (ROM), magnetic floppy disk, flash memory, and other types of memories, or a combination thereof. The present techniques may be implemented by patient signal analysis unit 122 that is stored in computer-readable media 105. As such, the computer system 101 is a general-purpose computer system that becomes a specific purpose computer system when executing the computer-readable program code.

The same or different computer-readable media 105 may be used for storing a database 124. Database 124 may include a repository of determined parameters and ratios, selectable predetermined functions, patient signal data, (e.g., electrophysiological, SPO2, respiration signal data, etc.), patient data (e.g., demographic data, pathology history, etc.), other input data and/or other derived output parameters. Patient signal data may be provided by a patient monitor 130 that is communicatively coupled to the computer system 101.

Patient monitor 130 may be used to acquire various types of patient biometric or physiological signal information for monitoring the patient. For example, the monitoring information may include, but is not limited to, electrophysiological signal data (e.g., ECG, ICEG, etc.), SPO2 signal data, respiration signal data, blood pressure, temperature and/or other patient biometric, physiological or medical parameter information. The patient monitor 130 may include appropriate biometric sensors (e.g., leads for surface ECG and catheter for intra-cardiac electrograms) for acquiring the monitoring patient signals. Implementations of the present framework provide sequential data modeling-based parameters to detect, diagnose and quantify such patient signals.

Figure 2:
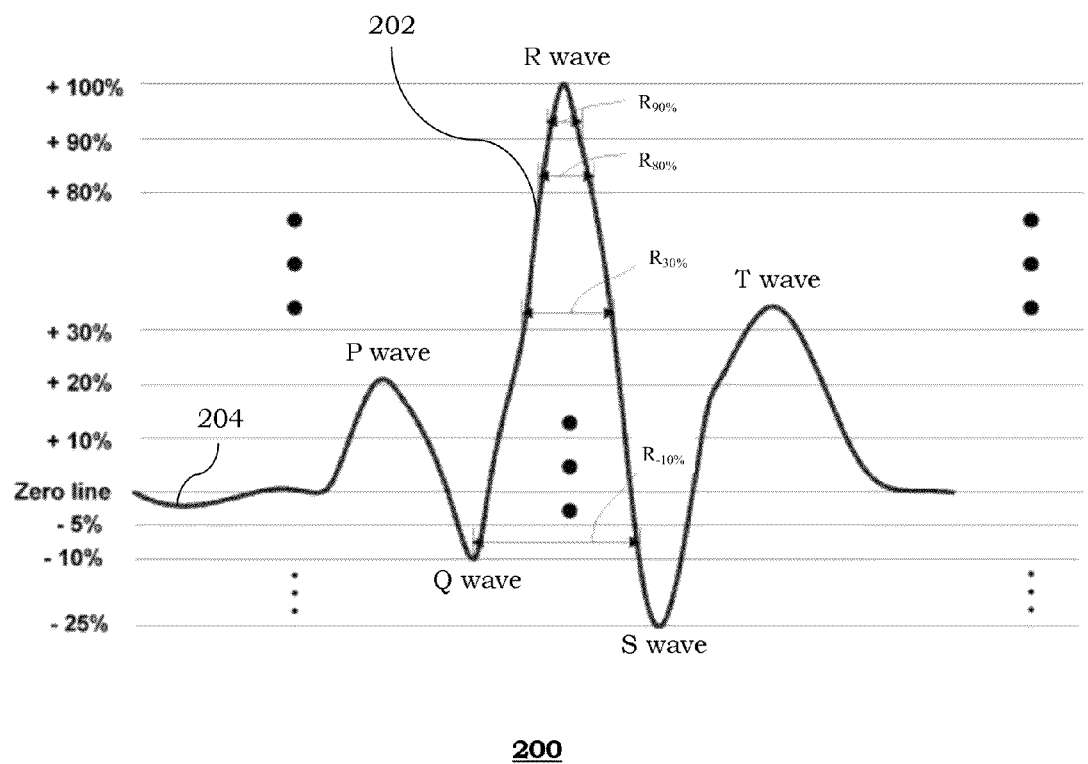
FIG. 2 is a schematic diagram illustrating an exemplary sequential morphology segmentation of cardiac ECG signal waveform.

FIG. 2 is a schematic diagram illustrating an exemplary sequential morphology segmentation of cardiac ECG signal waveform 200. Typically, a complete heart cycle of the ECG signal waveform 200 includes a P wave, Q wave, R wave, S wave, T wave, QRS complex, etc. Upon the emergence of a cardiac disease, the corresponding portion of the cardiac response signal portion will show some changes and distortions in morphology or shape, such as size, amplitude, timing, latency of corresponding signal peak, etc. However, usually in the early stage of the disease, these small changes are not easily detected and characterized by human vision. In addition, in most early stages of cardiac malfunctions, only part of the cardiac tissue is in irregular electrophysiological excitation. The overall shape or morphology of the waveform may change due to cardiac atrial or ventricular depolarization and repolarization.

Traditional clinical approaches focus mainly on the amplitude (e.g., max, average or min) and waveform peak position or latency to detect cardiac events. However, such approaches cannot detect early waveform morphology changes and distortions effectively and efficiently. In accordance with some implementations of the present framework, the ECG signal waveform 200 is segmented (or categorized) to derive a sequential morphological data series (or sequential time interval data). For instance, as shown in FIG. 2, the QRS complex segment 202 may further be segmented into different portions based on the percentage of the R wave maximum amplitude, such as +10%, +20%, −5%, −10%, etc. The corresponding R wave signal morphology at each amplitude percentage level (or the time intervals for such wave morphology) may be denoted by $R_{x\%}$. For example, in FIG. 2, the sequential morphological data series $R_{10\%}$, $R_{20\%}$, $R_{30\%}$, etc. is the R waveform morphology segmented section time intervals. Some portions of the amplitude may be below the zero voltage line (or baseline value) 204, which means that the sequential data series is $R_{-10\%}$, $R_{-20\%}$, $R_{-30\%}$, etc. This concept may be extended to other segments (e.g., P wave) of the ECG signal waveform 200 of a heart cycle. Different techniques may be used to perform the sequential amplitude segmentation, as will be discussed in more details later.

Figure 3:
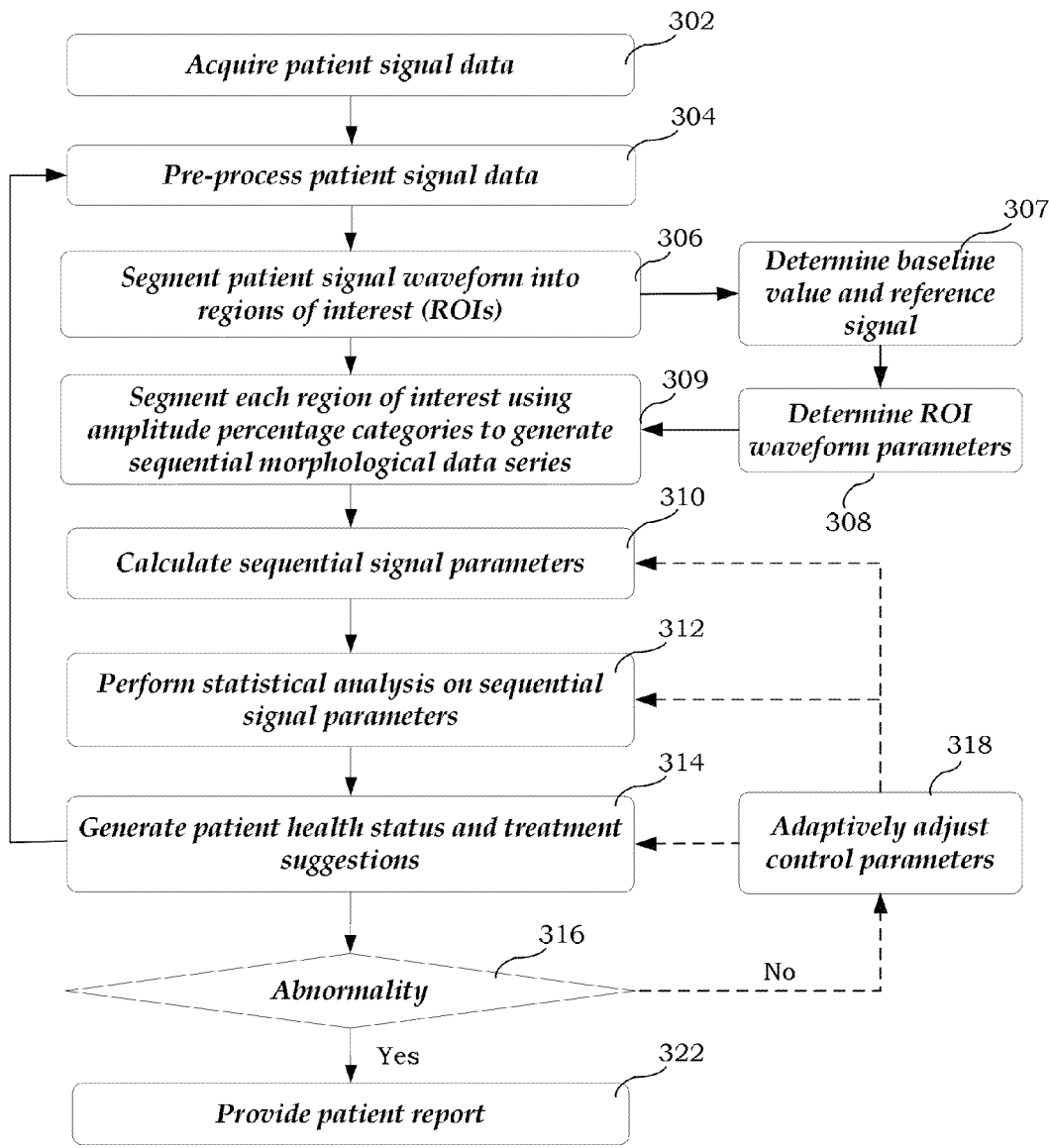
FIG. 3 shows an exemplary method of analyzing patient signals.

FIG. 3 shows an exemplary method 300 of analyzing patient signals based on sequential signal morphology segmentation. The steps of the method 300 may be performed in the order shown or a different order. Additional, different, or fewer steps may be provided. Further, the method 300 may be implemented with the system 100 of FIG. 1, a different system, or a combination thereof.

At 302, patient monitor 130 acquires patient signal data from a current patient. The patient signal data may be acquired over multiple successive cycles. Such patient signal data may include digitized data of electrophysiological signals, such as ECG or ICEG cardiac signals that indicate electrical activity of a patient's heart over multiple heart cycles. Other types of patient signals, such as hemodynamic (HEMO), oximetric (or SPO2), respiration (or capnographic), other vital sign signals and/or other measurable patient biometric, physiological or medical signals, may also be acquired. In addition, other patient information, such as demographic data, clinical application and patient status, including, but not limited to, weight, height, gender, age, allergies, medications, etc., may also be acquired.

At 304, patient monitor 130 pre-processes the patient signal data. Patient monitor 130 may pre-process the patient signals by filtering, amplification, digitization and/or buffering. For example, the patient signals may be pre-filtered and amplified for display on, for instance, patient monitor 130. The patient signals may be filtered to remove patient movement and respiratory artifacts, as well as power line noise. The filter may be adaptively selected in response to data indicating clinical application (e.g. ischemia detection application, rhythm analysis application). In some implementations, patient monitor 130 amplifies, buffers, filters and/or digitizes the patient signals to produce a continuous stream of digitized samples. The digitized patient signal samples or data are provided to patient signal analysis unit 122 for processing.

At 306, patient signal analysis unit 122 segments the waveform of the patient signal data into at least one region of interest (ROI) within a cycle. Such segmentation may be performed continuously and in real-time. In some implementations, an ROI is a graphical deflection commonly observed on a typical electrophysiological signal waveform. One or more types of ROIs may be identified. Examples of ROI types include, but are not limited to, the QRS complex segment, the P wave, the R wave, the Q wave, the T wave, and so forth. To segment the waveform, a peak and/or valley detector may be provided in the patient signal analysis unit 122 for detecting the start and end points of an ROI.

At 307, patient signal analysis unit 122 determines the baseline value and reference signal from the digitized patient signals. The baseline value (or level) generally refers to a known threshold value with which an unknown is compared when measured or assessed. The baseline value may comprise a zero voltage line if a static (DC) voltage signal component is filtered out from the signal. The baseline value may be automatically, semi-automatically or manually selected by the user. It may be selected and adaptively adjusted according to the current application and clinical requirements. The reference signal is a benign signal received from a healthy patient. In some implementations, the reference signal is segmented to identify a reference region of interest. The type of reference ROI corresponds to the type of ROIs identified in step 306 (e.g., P wave, R wave, QRS complex, etc.). Multiple ROIs corresponding to multiple cycles may be identified within a shifting window.

At 308, patient signal analysis unit 122 determines waveform parameters of the identified ROIs in the patient signal and the reference signal. Such waveform parameters may include, for example, the maximum amplitude, time durations, etc. For instance, in the case of a QRS complex-type of ROI, the maximum amplitude of the R wave may be measured from the baseline value. A timing detector may be provided in the patient signal analysis unit 122 for determining time durations of the ROIs. The timing detector may use a clock counter for counting a clock between start and end points, and the counting may be initiated and terminated in response to the detected start and end point characteristics.

At 309, patient signal analysis unit 122 segments the identified ROIs using amplitude percentage categories. Amplitude percentage categories may be derived from the reference ROI(s) identified from the reference signal in step 307. A sequential morphological data series may then be generated based on such segmented portions.

Figure 4A:
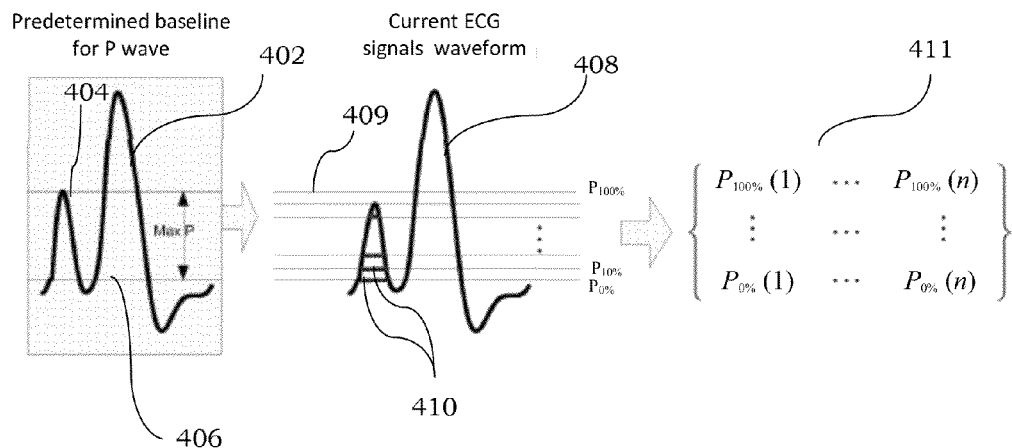
FIG. 4a illustrates an exemplary atrial fibrillation (AF) diagnostic method based on fixed P wave reference segmentation.
Figure 4B:
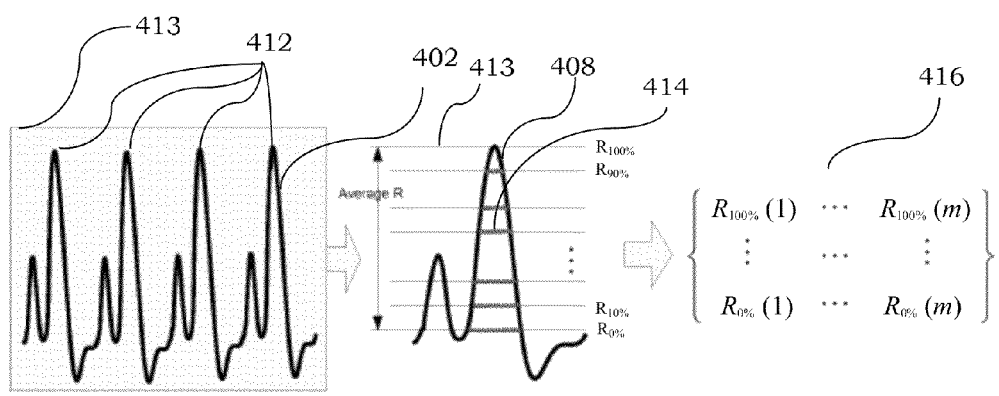
FIG. 4b illustrates an exemplary myocardial ischemia (MI) diagnostic method based on R wave average segmentation.

FIG. 4a illustrates an exemplary atrial fibrillation (AF) diagnostic method based on fixed P wave reference segmentation, while FIG. 4b illustrates a myocardial ischemia (MI)

diagnostic method based on R wave average segmentation. By using different calibration and segmentation methods, the corresponding sequential morphology data series (411 and 416) of the segmented time intervals may be derived, which may further be used for signal variation calculation and characterizing the severity, type and timing of cardiac arrhythmia. The different techniques illustrated by FIGS. 4*a-b* may be selected based on, for example, the clinical application needs and noise level. For instance, in a noisy environment, the multi-heart-cycle averaging method illustrated by FIG. 4*b* may be more useful. In addition, although the P and the R waves are illustrated in the following description, other segments or regions of interest (e.g., T wave, Q wave, S wave, etc.) may also be used.

Turning to FIG. 4*a*, a reference signal 402 may be segmented to identify the reference ROI, which is the P wave 404 in this example. The maximum amplitude (Max P) of the P wave from the baseline value 406 may be determined from a single cycle of the reference signal 402. Max P may be used to define various categories for segmenting the current ECG signal waveform 408. In some implementations, categories of amplitude 409 based on a percentage of Max P (e.g., $P_{0\%}$, $P_{10\%}$, $P_{20\%}$, ..., $P_{100\%}$) are defined. Although a 10-level segmentation is illustrated, it should be appreciated that the number of levels may be adjusted according to the needs of the clinical application, such as sensitivity and reliability requirements.

The ECG signal 408 from the current patient may be segmented based on these amplitude categories 409 into portions. The time intervals 410 of these portions (or amplitude percentage time intervals) are then compiled as a sequential morphological data series 411. For example, $P_{0\%}(1)$ denotes the time interval of the portion segmented by $P_{0\%}$ in the first cycle of the current ECG signal 408, $P_{100\%}(n)$ denotes the time interval of the portion segmented by $P_{100\%}$ in the nth cycle of the current ECG signal 408, and so forth. The letter n denotes the size of the data series 411, which may be adaptively and automatically adjusted by the user and/or system during real-time calculation and diagnosis by controlling the calculation window size.

FIG. 4*b* illustrates another exemplary segmentation method using an average maximum amplitude of multiple reference ROIs over a plurality of heart cycles (e.g., 2-10 heart cycles). As shown, a reference signal 402 may be segmented to identify reference R waves 412 over multiple heart cycles within a shifting window 413. The average maximum amplitude (Average R) of the R waves 412 may be determined from a heart cycle of the reference signal 402. Average R may be used to define various categories for segmenting the current ECG signal waveform 408. In some implementations, categories (or levels) of amplitude 413 (e.g., $R_{0\%}$, $R_{10\%}$, $R_{20\%}$, ... $R_{100\%}$) based on a percentage of Average R are defined. Although 10-level segmentation is illustrated, it should be appreciated that the number of levels may be adjusted according to the needs of the clinical application, such as sensitivity and reliability requirements.

The ECG signal 408 from the current patient may be segmented based on these amplitude categories 413 into portions. The time intervals 414 of these portions (or amplitude percentage time intervals) are then compiled as a sequential morphological data series 416. For example, $R_{0\%}(1)$ denotes the time interval of the portion segmented by $R_{0\%}$ in the first cycle of the current ECG signal 408, $R_{100\%}(m)$ denotes the time interval of the portion segmented by $R_{100\%}$ in the mth cycle of the current ECG signal 408, and so forth. The letter m denotes the size of the data series 416, which may be adaptively and automatically adjusted by the user and/or system during real-time calculation and diagnosis by controlling the calculation window size.

Turning back to FIG. 3, at 310, patient signal analysis unit 122 determines sequential signal parameters based on the sequential morphological data series. Examples of sequential signal parameters include, but are not limited to, sequential unilateral ratio (SUR), sequential cross unilateral ratio (SCUR), sequential bilateral ratio (SBR), sequential cross bilateral ratio (SCBR) and multi-ratio combination integrated index (or combined sequential ratio). These sequential signal parameters characterize the mode and pattern changes and distortions within the patient signal waveforms for use in, for example, diagnosing biomedical conditions.

In some implementations, a sequential unilateral ratio (SUR) is determined. SUR may be used to compare the different amplitude percentage time intervals within the same ROI of the same heart cycle of the current patient signal. More particularly, the SUR may be computed as follows:

$$SUR_{X-a-b}(N) = \frac{X_{a\%}(N)}{X_{b\%}(N)} \qquad (1)$$

wherein $SUR_{X-a-b}$ (N) denotes the sequential unilateral ratio of the ROI X for the current heart cycle N of the current patient signal (in this way, each heart cycle may be evaluated continuously and substantially in real-time as the patient signal is acquired); $X_{a\%}$ refers to the corresponding time interval of the portion of ROI X segmented by a % amplitude percentage category (e.g., $R_{10\%}$), while $X_{b\%}$ refers to the corresponding time interval of the portion of ROI X segmented by a different b % amplitude percentage category (e.g., $R_{20\%}$). By continuously monitoring the $SUR_{X-a-b}$ (N) in substantially real-time, the minute morphological changes and distortions of the patient signal may be qualitatively and quantitatively detected and characterized. The ROI X may be the P wave, R wave, T wave, Q wave, S wave, or any other segment of the same patient signal cycle.

In some implementations, a sequential cross unilateral ratio (SCUR) is determined. SCUR describes the relative changes between different ROIs of the same heart cycle of the current patient signal, such as the time interval ratio between the sequential data of the R wave and the P wave. In some implementations, the SCUR shows the relative signal morphology changes between two ROIs in the same heart cycle. In some implementations, the SCUR is computed as follows:

$$SCUR_{XY-a}(N) = \frac{X_{a\%}(N)}{Y_{a\%}(N)} \qquad (2)$$

wherein $SCUR_{XY-a}$ (IV) denotes the sequential cross unilateral ratio of the ROIs X and Y for the current heart cycle N of the current patient signal (in this way, each heart cycle may be evaluated continuously and substantially in real-time to detect differences between different ROIs of the same cardiac cycle); $X_{a\%}$ denotes the corresponding time interval of the portion of ROI X segmented by a % amplitude percentage category (e.g., $R_{10\%}$), while $Y_{a\%}$ refers to the corresponding time interval of the portion of a different ROI Y segmented by the same a % amplitude percentage category (e.g., $P_{10\%}$). In other words, this exemplary SCUR represents the cross ratio between different ROIs (X and Y) at the same amplitude level of signal segmentation. The ROIs X and Y may be the P wave, R wave, T wave, Q wave, S wave, or any other segment of the same patient signal cycle.

The SCUR may also be computed between different ROIs (X and Y) of the same heart cycle using time intervals of different amplitude percentage categories. In some implementations, the SCUR is computed as follows:

$$SCUR_{XY-a-b}(N) = \frac{X_{a\%}(N)}{Y_{b\%}(N)} \quad (3)$$

wherein $SCUR_{XY-a-b}$ (N) is the sequential cross unilateral ratio of different ROIs X and Y for the current heart cycle N at different percentage segmentations a % and b % (in this way, each heart cycle may be evaluated continuously in substantially real time to detect differences between the different ROIs of the same cardiac cycle); $X_{a\%}$ denotes the corresponding time interval of the portion of ROI X segmented by a % amplitude percentage category (e.g., $R_{10\%}$), while $Y_{b\%}$ refers to the corresponding time interval of the portion of a different ROI Y segmented by a different b % amplitude percentage category (e.g., $P_{20\%}$). In other words, this exemplary SCUR represents the cross ratio between different ROIs (X and Y) at different amplitude levels of signal segmentation.

In some implementations, a sequential bilateral ratio (SBR) is determined. The SBR characterizes morphology changes and distortions between different heart cycles. By comparing the same type of ROI from different heart cycles, for example, signal portion morphology changes may be detected earlier and more sensitively. The SBR may be computed as follows:

$$SBR_{X-a-b}(N) = \frac{X_{a\%}(N)}{X_{b\%}(M)} \quad (4)$$

or $$SBR_{X-a-b}(N) = \frac{X_{a\%}(M)}{X_{b\%}(N)} \quad (5)$$

wherein $SBR_{X-a-b}$ (N) is the sequential bilateral ratio of the same type of ROI X for the current heart cycle N; $X_{a\%}$ (N) and $X_{a\%}$ (M) denote the corresponding time intervals of the portions of ROI X segmented by a % amplitude percentage category (e.g., $R_{10\%}$) within heart cycles N and M respectively, while $X_{b\%}$ (M) and $X_{b\%}$ (IV) denote the corresponding time intervals of the portions of ROI X segmented by b % amplitude percentage category (e.g., $R_{20\%}$) within heart cycles M and N respectively. By using the sequential bilateral ratio $SBR_{X-a-b}$ (N), such as 10% segmented signal time interval of the R wave of the current heart cycle (N) and the 20% segmented signal time interval of the R wave from the previous heart cycle (M), the pathology (e.g., myocardial ischemia event) may be detected earlier and more reliably. The values of a % and b % may be selected based on, for example, the ROI signal noise ratio and the needs of the clinical application.

In some implementations, a sequential cross bilateral ratio (SCBR) is determined. The SCBR is useful for comparing two different ROIs within two different heart cycles at different amplitude levels of signal segmentation. The SCBR may be computed as follows:

$$SCBR_{XY-a-b}(N) = \frac{X_{a\%}(N)}{Y_{b\%}(M)} \quad (6)$$

or $$SCBR_{XY-a-b}(N) = \frac{X_{a\%}(M)}{X_{b\%}(N)} \quad (7)$$

wherein $SCBR_{X-a-b}$ (N) is the sequential cross bilateral ratio derived from the ratio between the time interval of ROI X of heart cycle N and time interval of ROI Y of heart cycle M; $X_{a\%}$ (N) and $X_{a\%}$ (M) denote the corresponding time intervals of the portions of ROI X segmented by a % amplitude percentage category (e.g., $R_{10\%}$) within heart cycles N and M respectively, while $Y_{b\%}$ (M) and $Y_{b\%}$ (N) denote the corresponding time intervals of the portions of ROI Y segmented by b % amplitude percentage category (e.g., $R_{20\%}$) within heart cycles M and N respectively. Such sequential cross bilateral ratio $SCBR_{X-a-b}$ (N) captures and detects the different ROIs across different heart cycles. The heart cycles (M and N) that are used for comparison may be selected adaptively and automatically by the system or the user.

In summary, the sequential signal ratios, as previously described, may be calculated and derived from the same ROI in the same heart cycle of the patient signal, from different ROIs in the same heart cycle, from different ROIs either in the same heart cycle or different heart cycles. Accordingly, there may be many different percentage segmented data for different ROIs, different percentage data series and different kinds of sequential signal ratios.

In some implementations, a multi-ratio combination integrated index is provided to integrate different sequential signal ratios. This may be performed to achieve real time continuous monitoring and characterization of patient signal waveform and morphology. A multi-ratio combination integrated index may be determined as follows:

$$\text{Combined\_sequential\_ratio}(N) = \sum_{i \in \Omega} \lambda_i \cdot \text{sequential\_ratio}(N)_i \quad (8)$$

wherein Combined_sequential_ratio (N) is the combination integrated index for current heart cycle N that combines different sequential signal ratios defined in equations (1) to (7) with coefficients $\lambda_i$ corresponding to each sequential signal ratio (sequential_ratio); and $\Omega$ denotes the data series set for all the sequential signal ratios that may be used for calculating the combination ratio.

The coefficient $\lambda_i$ for the sequential ratio combination index may be time varying. Accordingly, equation (8) may be rewritten as follows:

$$\text{Combined\_sequential\_ratio}(N) = \sum_{i \in \Omega} \lambda_i(N) \cdot \text{sequential\_ratio}(N)_i \quad (9)$$

In addition, the combination index may further be expanded into the following equation:

$$\text{Combined\_sequential\_ratio}(N) = \sum_{i \in \Omega} \lambda_i(N) \cdot \text{sequential\_ratio}(N)_i \quad (10)$$

$$= \sum_{i \in =\Phi 1} \alpha_i(N) \cdot SUR_{X-a-b}(N)_i +$$

$$\sum_{i \in \Phi 2} \beta_i(N) \cdot SCUR_{XY-a}(N)_i +$$

$$\sum_{i \in \Phi 3} \omega_i(N) \cdot SBR_{X-a-b}(N)_i +$$

$$\sum_{i \in \Phi 4} \theta_i(N) \cdot SCBR_{XY-a-b}(N)_i$$

wherein $\alpha_i$, $\beta_i$, $\omega_i$ and $\theta_i$ are coefficients for corresponding sequential signal ratios (these coefficients may be static or adaptively updated by the system or user). $\Phi 1$, $\Phi 2$, $\Phi 3$ and $\Phi 4$ are the data set of the different sequential signal ratios calculations of corresponding ratios. For example, all may include $SUR_{R\text{-}10\%\text{-}20\%}$, $SUR_{R\text{-}10\%\text{-}30\%}$, $SUR_{R\text{-}10\%\text{-}40\%}$, ..., $SUR_{P\text{-}20\%\text{-}10\%}$. Hence, with the combination index, any signal morphological changes, at any signal portion and signal timing, may be sensitively and reliably captured and characterized quantitatively. It may not be necessary to use all kinds of sequential signal ratios to compute the combination index. One, two or more of the ratios may be selected based on the clinical application to achieve optimal results.

At 312, patient signal analysis unit 122 performs statistical analysis on the determined sequential signal parameters. The statistical analysis may be performed by computing statistical parameters based on the determined sequential signal parameters to reliably quantify and compare the signal changes with a pre-determined threshold (e.g., relative changes). Examples of such statistical parameters include the mean value, standard deviation, variation and variability of the sequential ratio data series. Other types of statistical analysis, such as t-test hypothesis, may also be performed.

The sequential ratio variation and the sequential ratio variability may be defined to calculate the changing level of ratio calculation index series, which may then be used to, for example, characterize the severity, type and prediction of cardiac pathologies and events. In some implementations, the sequential ratio variation and variability are calculated as follows:

$$\text{Sequential\_Ratio\_Variation} = \frac{W\_mean(Ratio\_series)}{W\_STD(Ratio\_series)} \quad (11)$$

$$\text{Sequential\_Ratio\_Variability} = \quad (12)$$
$$\frac{W\_max(Ratio\_series - W\_mean(Ratio\_series))}{W\_mean(Ratio\_series)}$$

wherein W_mean and W_STD denote the mean value and standard deviation of the calculated ratio series in a user or system defined shifting window (e.g., 2-10 heart cycles; window size may be larger based on clinical application requirements and environment noise); W max is the maximum value of the ratio series within the shifting window.

At 314, patient signal analysis unit 122 generates patient health status and treatment suggestions based at least in part on the determined sequential signal parameters. In some implementations, different types of sequential signal parameters, associated statistical parameters and/or other input patient data are linearly or non-linearly combined to generate the patient health status, treatment suggestions, coefficients (e.g., $\alpha_i$, $\beta_i$, $\omega_i$, $\theta_i$, etc.) for calculating the sequential signal parameters, and/or other types of output. Different methods, such as an artificial neural network (ANN), fuzzy algorithm, etc., may be used to integrate the input patient data.

Figure 5:
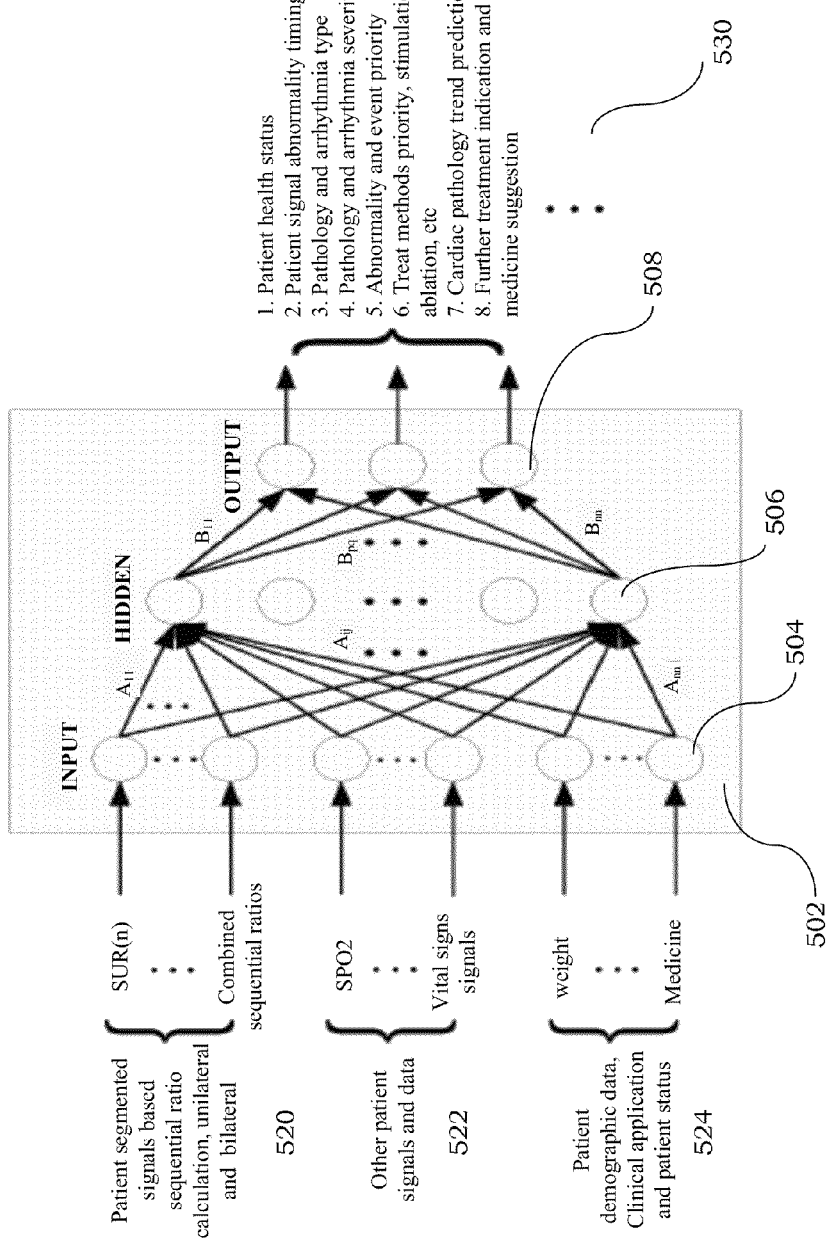
FIG. 5 shows an exemplary ANN structure for integrating multiple types of patient data.

FIG. 5 shows an exemplary ANN structure 502 for integrating multiple types of patient data for providing decision support in diagnosis and treatment of cardiac pathologies and arrhythmia and analysis of tissue function. In some implementations, sequential signal parameters derived from different kinds of clinical situations (e.g., rest, exercise, under medication, etc.) may also be retrieved from a patient database and used to train the ANN structure 502 to obtain substantially real-time, adaptively adjusted coefficients (e.g., $\alpha_i$, $\beta_i$, $\omega_i$, $\theta_i$, etc.) for different patient signal data for use in the sequential signal parameter calculations.

Exemplary ANN structure 502 includes three layers—input layer 504, hidden layer 506 and output layer 508—for combining and integrating different kinds of determined sequential signal parameters and/or associated statistical parameters 520, other patient signal data (e.g., HEMO, blood pressure, SPO2 and other vital sign signal data) 522 and patient status, demographic data, clinical application and other information (e.g., weight, height, medication, allergies, etc.) 524. ANN structure 502 combines and maps patient data 520, 522 and 524 to output parameters 530. Output parameters 530 may indicate, for example, estimated patient health status, estimated abnormality or pathology (e.g., arrhythmia) timing, type, severity and/or trend, abnormality and event priority, suggestions for methods of treatment (e.g., atrial fibrillation ablation priority, stimulation site decision, etc.), prediction of cardiac pathological trends, suggestions for further treatment indication and medication, and so forth. Such output parameters 530 may be used for the detection, diagnosis, warning and/or treatment of abnormalities. They may be used in different clinical applications, such as in operating room (OR) monitoring, ICU/CCU critical monitoring and emergency room (ER) patient status and health monitoring.

$A_{ij}$ are weights applied between the input layer 504 and hidden layer 506, while $B_{pq}$ are weights applied between hidden layer 506 and output layer 508 of the ANN computation. $A_{ij}$ weights and $B_{pq}$ weights are adaptively adjusted and tuned using a training data set. ANN unit 502 may incorporate a self-learning function that processes new input data 520, 522 and 524 to increase the precision and accuracy of calculated results. The exemplary ANN-based analysis may combine sequential signal parameters with information derived from a medical professional's experience (input and suggested controlling mode) to greatly improve the sensitivity, specificity, stability and reliability of non-invasive methods.

Turning back to FIG. 3, at 316, patient signal analysis unit 122 determines whether the patient has an abnormality. The abnormality may be, for example, a cardiac medical condition such as cardiac arrhythmia, cardiac tissue and electrophysiological-hemodynamic malfunctions, etc. The abnormality may be identified based on, for instance, threshold values.

If an abnormality is not identified, at 318, patient signal analysis unit 122 may optionally adaptively adjust calculation parameters used for calculating the afore-mentioned parameters. The adaptive adjustment may be performed automatically, semi-automatically or manually by the clinical user. Such calculation parameters include, but are not limited to, number of samples in a calculation window, coefficients, weights, time steps, thresholds, and so forth. In the case of ventricular arrhythmia analysis, a severity threshold, calculation time step and monitored tissue location may be selected in response to user command or automatic system adaptive adjustment.

If an abnormality is identified, the process 300 may proceed to step 322. At 322, patient signal analysis unit 122 outputs a patient report. The patient report may indicate the abnormality, associated characteristics (e.g., type, severity, timing, etc.) and other information (e.g., suggested treatment options). The patient report may be in the form of, for example, an alert message presented at patient monitor 130. The patient report may be stored in database 124 for future retrieval.

Some implementations of the present framework described herein may be used for detecting, calculating and/or estimating any type of cardiac pathology and arrhythmia in any clinical cases and events. A computer simulation was performed to compare the performance of some implementations of the present framework with a conventional technique used for myocardial ischemia detection and characterization.

Figure 6:
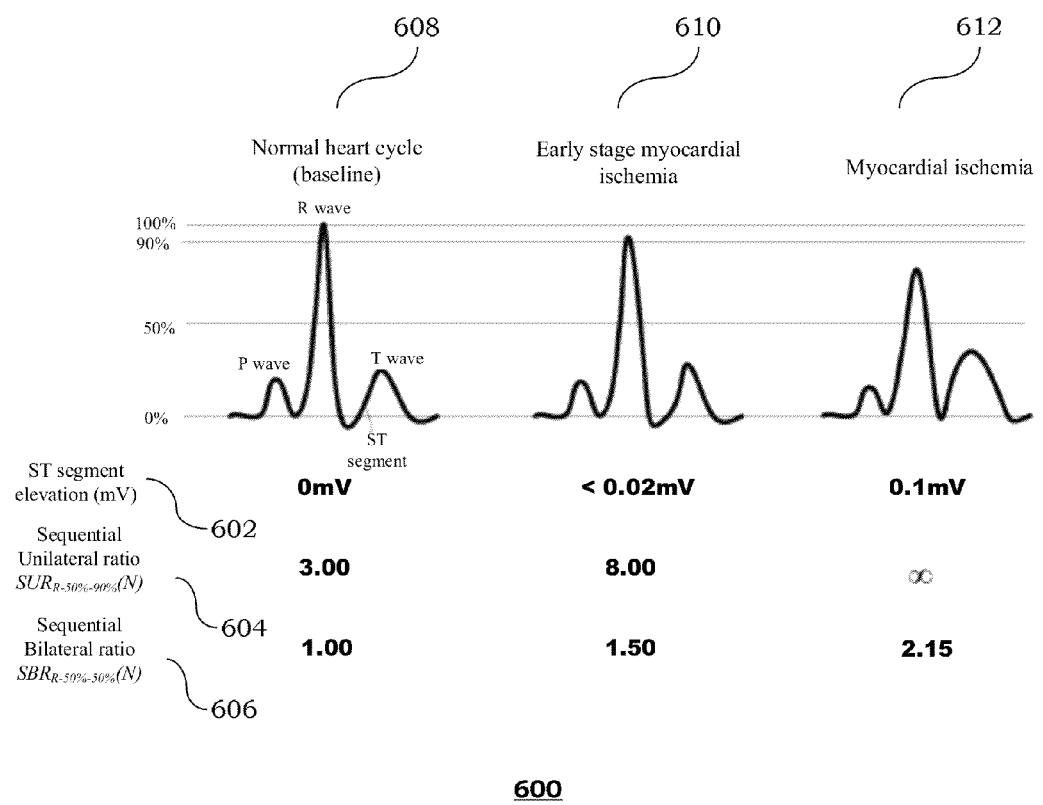
FIG. 6 shows a table that illustrates the results of a computer simulation.

FIG. 6 shows a table 600 that illustrates the results of the computer simulation. Results computed by a traditional clinical standard method based on ST segment elevation (602) and R wave sequential time interval series method based on sequential unilateral ratio (604) and bilateral ratio (606) with reference to a baseline normal heartbeat were compared. Three episodes of cardiac events were simulated: normal benign signal cycle (which is also used as the reference signal) (608); heart cycle of early stage of myocardial ischemia (610); and heart cycle during myocardial ischemia (612).

Using the traditional standard ST segment analysis (602), ischemia events can only be qualitatively detected: in the three episodes (608, 610, 612), the ST segment elevations are 0 mV, <0.02 mV and 0.1 mV respectively. Hence, ST segment diagnosis cannot really detect myocardial ischemia in the early stage (610). Using the sequential unilateral and bilateral ratios computed according to the techniques described herein, however, the myocardial ischemia event may be both qualitatively and quantitatively detected and characterized.

More particularly, by using the sequential unilateral ratio $SUR_{R-50\%-90\%}$ (N), which compares the time intervals for 50% and 90% amplitude segmented R wave portions, the ratios for the three episodes are 3.00, 8.00 and ∞. These ratios describes the occurrence of myocardial ischemia very well, since they show distinct variations in the three episodes, with more than 200% change in value for the early stage (610). Similarly, by using the sequential bilateral ratio $SBR_{R-50\%-50\%}$ (N), which compares the 50% amplitude segmented R waveform time intervals between the current heart cycle and normal cardiac heart cycle in the baseline, the ratios for the three episodes are 1.00, 1.50 and 2.15. These ratios also show distinct variations in the three episodes, with 50% change in value for the early stage (610). Accordingly, these simulation results show that the sequential signal parameters derived in accordance with the present framework provide a more sensitive and efficient real time data diagnosis for cardiac abnormalities. By selecting the ROI for computing the sequential signal parameters, specificity in the cardiac arrhythmia detection may also be efficiently achieved. In addition, the ischemia event trend, severity, timing and/or other characteristics may also be easily generated.

While the present invention has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

The invention claimed is:

1. A method of patient signal analysis, comprising:
 receiving patient signal data;
 identifying at least one region of interest within a cycle of a waveform of the patient signal data;
 segmenting the identified region of interest into portions using amplitude percentage categories;
 generating a sequential morphological data series by compiling time intervals of the segmented portions;
 calculating one or more sequential signal parameters based on the sequential morphological data series; and
 generating a report based at least in part on the one or more sequential signal parameters.

2. The method of claim 1 wherein receiving patient signal data comprises receiving electrophysiological signal data that indicate electrical activity of a patient's heart over multiple heart cycles.

3. The method of claim 1 wherein the region of interest comprises a QRS complex segment, an ST segment, a P wave, a R wave, a T wave, a Q wave, an S wave, or a combination thereof.

4. The method of claim 1 further comprising deriving the amplitude percentage categories from at least one corresponding reference region of interest of a reference signal.

5. The method of claim 4 wherein deriving the amplitude percentage categories comprises:
 determining a maximum amplitude of the reference region of interest; and
 defining the amplitude percentage categories based on percentages of the maximum amplitude.

6. The method of claim 4 wherein deriving the amplitude percentage categories comprises:
 determining an average maximum amplitude of multiple reference regions of interest of the reference signal; and
 defining the amplitude percentage categories based on percentages of the average maximum amplitude.

7. The method of claim 1 wherein calculating the one or more sequential signal parameters comprises calculating a sequential unilateral ratio.

8. The method of claim 1 wherein calculating the one or more sequential signal parameters comprises calculating a sequential cross unilateral ratio.

9. The method of claim 1 wherein calculating the one or more sequential signal parameters comprises calculating a sequential bilateral ratio.

10. The method of claim 1 wherein calculating the one or more sequential signal parameters comprises calculating a sequential cross bilateral ratio.

11. The method of claim 1 wherein calculating the one or more sequential signal parameters comprises calculating a multi-ratio combination integrated index based on at least two of sequential unilateral ratio, sequential cross unilateral ratio, sequential bilateral ratio and sequential cross bilateral ratio.

12. The method of claim 1 further comprising performing statistical analysis on a series of the one or more sequential signal parameters.

13. The method of claim 12 wherein performing statistical analysis comprises generating a mean value, a standard deviation, a variation, a variability, or a combination thereof of the series of the one or more sequential signal parameters.

14. The method of claim 1 further comprising generating a health status or treatment suggestion based at least in part on the one or more sequential signal parameters.

15. The method of claim 14 wherein generating the health status or treatment suggestion comprises combining, via an artificial neural network, different types of sequential signal parameters to generate the health status or treatment suggestion.

16. The method of claim 14 wherein generating the health status or treatment suggestion comprises combining, via an artificial neural network, the one or more sequential signal parameters with other input patient data to generate the health status or treatment suggestion.

17. The method of claim 1 further comprising adaptively adjusting coefficients for use in calculating the one or more sequential signal parameters.

18. The method of claim 1 wherein generating the report based at least in part on the one or more sequential signal parameters comprises generating the report indicating characteristics of cardiac arrhythmia.

19. A non-transitory computer readable medium embodying a program of instructions executable by machine to perform steps for heart function analysis, the steps comprising:
   receiving patient signal data;
   identifying at least one region of interest within a cycle of a waveform of the patient signal data;
   segmenting the identified region of interest into portions using amplitude percentage categories;
   generating a sequential morphological data series by compiling time intervals of the segmented portions;
   calculating one or more sequential signal parameters based on the sequential morphological data series; and
   characterizing cardiac arrhythmia based at least in part on the one or more sequential signal parameters.

20. A system for patient signal analysis, comprising:
   a non-transitory memory device for storing computer readable program code; and
   a processor in communication with the memory device, the processor being operative with the computer readable program code to perform steps comprising:
   receiving patient signal data;
   identifying at least one region of interest within a cycle of a waveform of the patient signal data;
   segmenting the identified region of interest into portions using amplitude percentage categories;
   generating a sequential morphological data series by compiling time intervals of the segmented portions;
   calculating one or more sequential signal parameters based on the sequential morphological data series; and
   generating a report based at least in part on the one or more sequential signal parameters.

* * * * *